United States Patent
Marganski et al.

(10) Patent No.: US 7,253,002 B2
(45) Date of Patent: Aug. 7, 2007

(54) FLUID STORAGE AND DISPENSING VESSELS HAVING COLORIMETRICALLY VERIFIABLE LEAK-TIGHTNESS, AND METHOD OF MAKING SAME

(75) Inventors: Paul J. Marganski, Seymour, CT (US); Jose I. Arno, Brookfield, CT (US); Edward A. Sturm, New Milford, CT (US); Kristy L. Zaleta, Danbury, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 216 days.

(21) Appl. No.: 10/699,863

(22) Filed: Nov. 3, 2003

(65) Prior Publication Data

US 2005/0092761 A1    May 5, 2005

(51) Int. Cl.
*G01N 31/22* (2006.01)
(52) U.S. Cl. ............................................... 436/3
(58) Field of Classification Search ............... 436/3, 436/180; 422/100
See application file for complete search history.

(56) References Cited

U.S. PATENT DOCUMENTS

| | | | | |
|---|---|---|---|---|
| 3,854,885 A | * | 12/1974 | Fromm et al. ............... | 422/86 |
| 4,106,428 A | * | 8/1978 | Matthiessen ................ | 116/200 |
| 4,288,402 A | * | 9/1981 | Ellis ............................ | 422/61 |
| 4,408,480 A | * | 10/1983 | Christie ...................... | 73/40.7 |
| 4,673,652 A | * | 6/1987 | McStravick et al. ........... | 436/2 |
| 4,690,865 A | | 9/1987 | Fong | |
| 4,748,930 A | * | 6/1988 | Leichnitz ................... | 116/206 |
| 4,756,415 A | * | 7/1988 | Call ........................... | 206/703 |
| 4,770,028 A | * | 9/1988 | Flippo, Jr. ................... | 73/40.7 |
| 4,784,959 A | * | 11/1988 | Wegrzyn ...................... | 436/3 |
| 4,786,561 A | | 11/1988 | Fong | |
| 4,822,743 A | * | 4/1989 | Wegrzyn ...................... | 436/3 |
| 4,827,944 A | * | 5/1989 | Nugent ...................... | 600/584 |
| 4,828,790 A | * | 5/1989 | Honda et al. ................ | 376/306 |
| 4,913,927 A | * | 4/1990 | Anderson .................... | 427/580 |
| 4,927,708 A | * | 5/1990 | Herran et al. ............... | 428/332 |
| 4,952,451 A | * | 8/1990 | Mueller ...................... | 428/218 |
| 4,958,895 A | * | 9/1990 | Wells et al. ................ | 385/130 |
| 5,108,803 A | * | 4/1992 | Kondo et al. .............. | 428/34.2 |
| 5,322,797 A | * | 6/1994 | Mallow et al. ............. | 436/106 |
| 5,352,517 A | * | 10/1994 | Clough et al. .............. | 428/357 |
| 5,447,688 A | * | 9/1995 | Moore .......................... | 422/56 |
| 5,468,597 A | * | 11/1995 | Calabrese et al. .......... | 430/315 |

(Continued)

FOREIGN PATENT DOCUMENTS

EP    1431734 A1    6/2004

(Continued)

*Primary Examiner*—Brian R. Gordon
(74) *Attorney, Agent, or Firm*—Steven J. Hultquist; Intellectual Property/ Technology Law; Margaret Chappuis (57) ABSTRACT

A chemical storage and dispensing vessel having associated therewith a colorimetric member that is effective to change color in exposure to leakage of a gas contained in the vessel. The colorimetric member may be constituted by a film, e.g., of a shrink-wrap character, that contains or is otherwise associated with a colorimetric agent undergoing color change in exposure to fluid leaking from the vessel. Such shrink-wrap film may be applied to a portion of the vessel susceptible to leakage, or alternatively to the entire vessel, so that the film is colorimetric effective to indicate the occurrence of a leakage event by visually perceptible change of color.

38 Claims, 3 Drawing Sheets

U.S. PATENT DOCUMENTS

| | | | |
|---|---|---|---|
| 5,518,528 A | 5/1996 | Tom et al. | |
| 5,657,910 A * | 8/1997 | Keyser | 222/382 |
| 5,755,175 A * | 5/1998 | White et al. | 116/206 |
| 5,856,172 A * | 1/1999 | Greenwood et al. | 435/260 |
| 6,089,027 A | 7/2000 | Wang et al. | |
| 6,093,572 A * | 7/2000 | Stenholm et al. | 436/1 |
| 6,101,816 A | 8/2000 | Wang et al. | |
| 6,322,920 B1 * | 11/2001 | Tomson | 429/34 |
| 6,323,032 B1 * | 11/2001 | Kuepper et al. | 436/1 |
| 6,342,281 B2 | 1/2002 | Hayakawa et al. | |
| 6,343,476 B1 | 2/2002 | Wang et al. | |
| 6,495,224 B1 | 12/2002 | Dutton | |
| 6,732,571 B1 * | 5/2004 | Flosbach | 73/40 |
| 6,790,763 B2 * | 9/2004 | Kondo et al. | 438/622 |
| 2003/0178337 A1 * | 9/2003 | Friedman | 206/497 |
| 2004/0075218 A1 * | 4/2004 | Heinzen | 277/321 |
| 2004/0115818 A1 * | 6/2004 | Puri et al. | 436/3 |
| 2004/0161529 A1 * | 8/2004 | Hongo et al. | 427/58 |
| 2004/0211667 A1 * | 10/2004 | Sberveglieri et al. | 204/426 |

FOREIGN PATENT DOCUMENTS

| | | |
|---|---|---|
| EP | 1 489 349 A1 | 12/2004 |
| EP | 1 489 350 A2 | 12/2004 |

\* cited by examiner

FLUID STORAGE AND DISPENSING VESSELS HAVING COLORIMETRICALLY VERIFIABLE LEAK-TIGHTNESS, AND METHOD OF MAKING SAME

BACKGROUND OF THE INVENTION

1. Field of the Invention

The present invention relates to storage and dispensing vessels such as are utilized for storage, transport and dispensing of materials in semiconductor manufacturing operations. More specifically, the invention relates to a secondary package for storage and dispensing vessels as well as to a method of making vessels having a secondary package.

2. Description of the Related Art

Vessels of widely varying types are extensively utilized in chemical industries, including semiconductor manufacturing, where liquid containers, gas cylinders and other types of material packages are used to supply reagents such as hydrides, halides, organometallic compounds, etc. to semiconductor manufacturing tools.

In the field of semiconductor manufacturing, new packaging approaches have been developed in recent years, including low pressure adsorbent-based fluid storage and dispensing vessels of the type disclosed in Tom et al. U.S. Pat. No. 5,518,528, as commercially available from ATMI, Inc. (Danbury, Conn.) under the trademark "SDS," and pressure-regulated fluid storage and dispensing vessels of the type described in Wang et al. U.S. Pat. No. 6,101,816, Wang et al. U.S. Pat. No. 6,089,027 and Wang et al. U.S. Pat. No. 6,343,476, as commercially available from ATMI, Inc. (Danbury, Conn.) under the trademark "VAC." Regardless of the specific type of material storage and dispensing vessel employed in a given material-consuming operation, it is necessary to maintain complete structural integrity in the storage, transport and deployment of such vessels, so that no leakage of contained material takes place, such as by leakage through couplings, valve head fittings, burst disks or other pressure relief devices associated with the vessel, seams, ports or other joints where welds or bonding media may fail and result in release of material from the vessel, etc.

The foregoing considerations are particularly acute where the contained material is very expensive, as in the microelectronics industry, where chemical reagents must be in many cases >99.999% pure in order to achieve reliability and acceptability of the product integrated circuitry that is manufactured using such chemical reagents. The foregoing also applies where the contained material is toxic or hazardous in character, and leakage may compromise human health and safety, or otherwise produce injury or adverse impact on the environment, or to the process facility in which the material is to be utilized.

For these reasons, it is common practice in the field of industrial containment to subject storage and dispensing vessels to leak-testing procedures, e.g., at the time that they are filled with material and sealed to provide the product package of material for subsequent use.

Although such point-of-origin testing of the leak-tightness of the storage and dispensing vessel may be effective to detect so-called "leakers," which then can be isolated and reworked or otherwise appropriately processed, there remains the potential during subsequent transport, storage and installation, for damage to occur to the vessel, that may compromise its structural integrity and leak-tightness.

For example, conventional gas cylinders are typically transported in bulk arrays that are strapped or secured together for transportation by truck, railcar, etc. In this condition, the vessels are subjected to shock, vibration, and impact, during their transport any intervening storage and final installation. Additionally, differential thermal effects may be significant, such as where such gas cylinders are transported by truck or railcar in long-haul operations, during which variations of temperature and humidity may adversely affect the structural integrity of the vessel and mediate leakage of fluid from the compromised vessel.

The foregoing potential for leakage is ameliorated to some extent by low-pressure packaging and dispensing of fluids, such as in the aforementioned SDS® and VAC® vessels, but nonetheless remains a significant risk in the transport, storage and installation of such vessels. It would therefore be a substantial advance in the art to markedly increase the safety characteristics of material storage and dispensing vessels, with respect to the occurrence of leakage events.

SUMMARY OF THE INVENTION

The present invention relates to storage and dispensing systems, such as are utilized to store, transport and deliver industrial solids, gases and liquids. More specifically, the present invention relates to such system, including apparatus and methods for visually detecting the occurrence of leaks from a storage and dispensing vessel.

In a further aspect, the present invention relates to a chemical storage and dispensing apparatus, comprising a chemical storage and dispensing vessel having associated therewith a colorimetric member effective in exposure to material leaking from the vessel to change color, thereby providing a visually perceptible response to a leakage event.

In another aspect, the present invention relates to a method of visually detecting a leakage event associated with a chemical storage and dispensing vessel, said method comprising disposing in chemical leakage detection proximity to the vessel a colorimetric member effective to undergo color change in exposure to leaking fluid from the vessel.

Additional aspects, features and embodiments of the invention will be more fully apparent from the ensuing disclosure and appended claims.

DETAILED DESCRIPTION OF THE DRAWINGS

DETAILED DESCRIPTION OF THE INVENTION AND PREFERRED EMBODIMENTS THEREOF

The present invention is based on the use of a colorimetric indicating medium associated with a chemical storage and dispensing vessel, which is deployed in close proximity to and as an integral structural component of the vessel assembly, to provide a visually perceptible indication of the occurrence of a leakage event, e.g., as may be attributable to vessel rupture, valve head leakage, deterioration of a burst disk or other pressure relief device, or other material failure or component failure that produces an undesired release of material from the vessel.

In one embodiment, the invention utilizes a colorimetric member at a portion of a chemical storage and dispensing vessel that is potentially susceptible to chemical leakage, so that a color change incident to undesired chemical release is visually discernable at a glance or by routine visual inspection. For example, the colorimetric member may comprise a web or sheet-form material, such as paper, cardboard, fiber board, felt, non-woven or woven materials, films, polymeric sheet stock or the like, which is impregnated with or otherwise includes a colorimetric agent that in exposure to the chemical contained in the vessel (upon leakage thereof) undergoes a color change to indicate the egress of chemical and the occurrence of an undesired leakage event.

In a further embodiment, the invention utilizes a colorimetric member at a portion of a fluid storage and dispensing vessel that is potentially susceptible to fluid leakage, so that a color change incident to undesired fluid release is visually discernable at a glance or by routine visual inspection. For example, the colorimetric member may comprise a web or sheet-form material, such as paper, cardboard, fiber board, felt, non-woven or woven materials, films, polymeric sheet stock or the like, which is impregnated with or otherwise includes a colorimetric agent that in exposure to the fluid contained in the vessel (upon leakage thereof) undergoes a color change to indicate the egress of fluid and the occurrence of an undesired leakage event.

For example, such colorimetric article may be disposed in proximity to the valve head of a pressurized fluid cylinder, on the valve head itself, or within a valve head cap or other "head" structure of the vessel, to provide a visually perceptible color indication of whether or not leakage has occurred from the vessel.

In another embodiment, the fluid storage and dispensing vessel is at least partially shrouded in a colorimetric film material, such as a heat-shrinkable wrap material impregnated with or otherwise including a colorimetric agent that undergoes color change in exposure to the fluid species of interest, as deriving from the bulk volume of fluid contained in the vessel.

In another embodiment, the colorimetric heat-shrinkable wrap film is applied over the head portion of a fluid storage and dispensing vessel, e.g., over the valve head and neck/shoulder region of the vessel.

In yet another embodiment, the colorimetric heat-shrink film is employed to completely wrap the vessel, so as to provide a fully shrouded vessel in which the shrink-wrap film enveloping the vessel provides a supplemental containment structure for the vessel, so that any leakage that occurs is contained within the shrink-wrap film envelope overlying the vessel, while at the same time the heat-shrink wrap film undergoes a colorimetric change upon contact with the leaking gas, to visually indicate that a leakage event has occurred.

The heat-shrink wrap film utilized for such purpose may be of any suitable type. Useful heat shrink film materials include polyvinyl chlorides (PVC), polyethylene, polypropylene, polyester, polyethylene/polypropylene copolymers, etc. The heat-shrink film materials may contain additives conferring heat-shrink character to the material. Such additives include plasticizers, which under heating conditions cause contraction of the film to conform same to the shape and surface(s) of an article on which the film is overlaid.

Polyethylene heat-shrink film is relatively inexpensive, and has a thickness that is typically on the order of 1.0 mil and higher. Polyolefin films are commercially available in differing compositions and multi-layer forms, with such films being readily modifiable within the skill of the art to provide suitable tearing resistance, zippering control, shrink control and other appropriate properties for the shrink wrap application. PVC heat-shrink films include heat-shrink films having very low shrink force characteristics, which are amenable to high-throughput manufacturing.

The foregoing heat-shrink films may be applied to chemical storage and dispensing vessels with conventional shrink wrap machines, including L-sealers and shrink tunnels, shrink wrap systems with heat guns, tray sealing machines, continuous band sealers, vacuum sealers, and the like, as utilized in heat-shrink operations involving food, consumer products, and the like.

The choice of a specific shrink wrap material will be determined by the heat-shrink equipment desired to be employed, as well as the cost, strength, shrink force, shrink temperature, heat-shrink dwell times (at the shrink temperature), etc.

The heat shrink film utilized in the practice of the present invention is preferably clear or translucent in character, in order to facilitate observation of the underlying fluid storage and dispensing vessel (e.g., to verify absence of damage, maintenance of mechanical integrity, etc.), but the film alternatively may be of an opaque character, so long as the colorimetric change incident to gas leakage is readily visually perceptible by an observer.

Heat-shrink wrap materials usefully employed in the broad practice of the present invention thus include the aforementioned polyethylene, PVC, polyolefin, and copolymer films, as well as the film materials disclosed in U.S. Pat. No. 4,786,561 ("Heat-Shrinkable Polymeric Barrier Film"), U.S. Pat. No. 4,690,865 ("Heat-Shrinkable Barrier Film"), U.S. Pat. No. 6,342,281 ("Heat-Shrinkable Polyester Films") and U.S. Pat. No. 6,495,224 ("Functionally Enhanced Protective Shrink-Wrap Coverings and Methods for their Manufacture and Use").

In accordance with a preferred aspect of the invention, the heat-shrink film is impregnated with or otherwise includes a colorimetric agent that in exposure to the fluid species contained in the vessel undergoes a color change to evidence the undesired leakage. For such purpose, the heat-shrink film may be coated with the colorimetric agent on an interior or fluid-contacting side of the film (as opposed to the outer, ambient environment-contacting side of the film), or the colorimetric agent may be formulated in or blended with the film material during its formation, so as to provide a film with homogeneous character that responds to contact with the target gas species by undergoing the desired color change. Alternatively, the shrink-wrap film may be transparent and simply provide a shroud or envelope structure enclosing the potential leakage site of the fluid storage and dispensing vessel, with the colorimetric member being disposed within such shroud or envelope, to provide a visualizable color change indicative of fluid leakage, as visible through the shrink-wrap film material.

The color change may be of any suitable character providing visual evidence to a viewer that the leakage event has occurred. Accordingly, any spectral colors of the virgin or originally provided film that are differentiable visually from the target gas-contacted film may be utilized. Examples of colorimetric agents that may be employed in the broad practice of the present invention include, in specific embodiments, iron oxide, copper sulfate, copper hydroxide, copper carbonate and the like, as well as pH indicating solutions, when the fluid species in the vessel is an acid gas. For detection of hydride gases, colorimetric agents such as copper sulfate, copper hydroxide and copper carbonate can be used. Colorimetric detection agents for fluoride gases can include iron oxide or other acid gas indicators.

As a specific example of a color-indicating shrink wrap film, the film may be a solvent-cast film, such as a polyvinyl alcohol (PVA) film, polyvinyl chloride (PVC) film, polycarbonate film, polyamide film, etc., which is cast from a solution or a dispersion of the polymer resin in a suitable solvent, e.g., aqueous medium such as water, organic solvent such as acetone, aniline, dimethyl sulfoxide (DMSO), benzene, dimethyl formamide (DMF), methyl ethyl ketone (MEK), ethyl acetate, ethylene dichloride, toluene, tetrahydrofuran (THF), etc. The colorimetric chemistry can be incorporated in the solvent casting formulation, so that the colorimetric chemistry is present as a component of the product film, or alternatively the film may be formed by solvent casting and the colorimetric chemistry can be applied to the film, either as a wet film or as a subsequently dried film, so that the colorimetric agent(s) are incorporated into the film material and therefore function thereafter to colorimetric indicate the presence of the target gas species to which the film is colorimetric sensitive.

As a further specific example, a PVA film can be cast from a solution of PVA in diethyl ether or acetone, to which copper sulfate has been added, with such precursor solution containing 15-20% by weight of PVA, based on the total weight of the solution, at sufficient wet film thickness to produce a dried film of 5-6 mils thickness. The film can be cast on a low surface energy substrate, e.g., a substrate coated with polytetrafluoroethylene, permitting the PVA film impregnated with the copper sulfide (as a hydride gas colorimetric agent) to be peeled from such substrate and thereafter used as a heat-shrink film to enshroud the fluid storage and dispensing vessel. Once the vessel, including the valve head assembly, is fully enshrouded in the shrink-wrap film, any subsequent leakage of hydride gas e.g., arsine, from the fluid storage vessel will change the film from bluish-white in color to black.

Alternatively, the film may be blow-molded, roto-molded, or formed in any other suitable manner.

As a further specific example, when the chemical in a fluid storage and dispensing vessel is tris(trifluoromethyl) stibine, the heat-shrink film may be formed of poly(vinyl pyridine), with the product film being yellow in color. In the event of leakage from the vessel of tris(trifluoromethyl) stibine, the film changes very rapidly to a bright red color, providing a visual verification of the leakage event.

Figure 1:
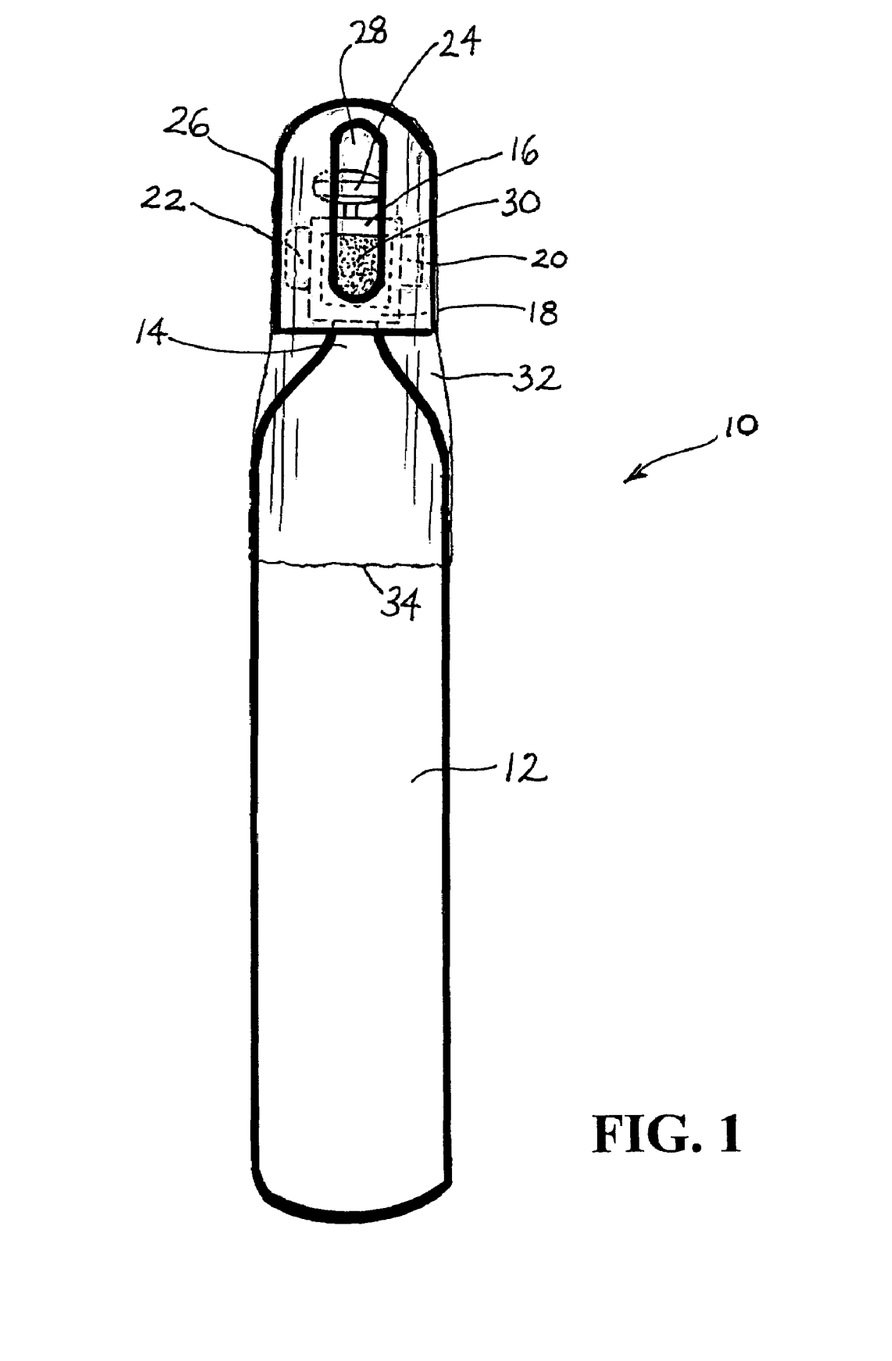
FIG. 1 is a front elevation view of a gas cylinder with colorimetric leak-indication elements, according to one embodiment of the invention.

Referring now to the drawings, FIG. 1 is a front elevation view of a gas storage and dispensing cylinder 10, including an elongate cylindrical vessel 12 whose upper portion includes a tapered neck 14 of reduced diameter, to which is attached a valve head 16.

The valve head 16 includes a block-like valve head body 18 containing interior gas flow passages communicating with an outlet port 20 and a burst disk 22. The valve head body 18 is operatively coupled with a manual hand wheel 24 that may be turned in respective opposing directions, to open an interior valve element (not shown in FIG. 1) for selective dispensing of gas from the cylinder, or alternatively to terminate flow by closure of the valve in the valve block body 18.

The burst disk 22 may be constructed and arranged to release the gas contents of the cylinder in the event of fire or other catastrophic condition resulting in over-pressure in the cylinder that approaches/exceeds the maximum use pressure for the cylinder.

Overlying the valve head assembly, including the valve block-associated elements, is a valve head cover 26. The valve head cover is removably coupled with the valve head assembly, to protect the valve head assembly during storage, transportation, installation and use of the cylinder.

The valve head cover 26 may as shown be provided with side openings 28 therein, as conventionally employed to allow dissipation of any leakage gas, e.g., to avoid build-up of hazardous concentrations of the gas, and to facilitate blowing out the interior volume enclosed by the cover, when the leaking cylinder is isolated for quarantine, reworking or disposal purposes.

In accordance with one embodiment of the invention, a colorimetric sheet-form element 30 is disposed on a flat surface of the valve head block 18. Such sheet-form element 30 may for example comprise a cellulosic (paper) sheet, or other mat or web element, impregnated or otherwise including the colorimetric agent that undergoes color change in exposure to the gas held in the vessel 12, in the event of a leakage occurrence.

The openings 28 in cover 26 therefore facilitate visual inspection of the colorimetric element and verification of the occurrence of a leakage event.

As an optional further feature of this embodiment of the invention, the upper portion of the cylinder 10 may be shrouded with a film 32 to enclose and overlie the upper portion of the vessel. In one specific embodiment, the film 32 is a heat-shrink film that is applied to the vessel and then subjected to appropriate heat-shrinking temperature conditions, to cause the film 32 to conform to the exterior surfaces of cover 26 and vessel 12, as shown. The film 32 may as illustrated enshroud the upper portion of the cylinder, terminating at a lower skirt edge 34, or alternatively the film 32 may be deployed so as to enshroud the entire body of the cylinder 10.

It will be appreciated that by the deployment of the shrink-wrap film 32 as shown in FIG. 1, a local environment is created beneath the film, in which any leakage gas will accumulate and serve to effect the colorimetric change of the film.

Additionally, such arrangement will enable the film 32 to contain any leakage of gas, so that the film thereby serves as a secondary containment vessel shrouding the portion of the cylinder that is most susceptible to leakage.

Since the film 32 is of a heat-shrink character, the lower portion of the film will be circumferentially in a compressive state against the exterior surface of the vessel, just below the neck and shoulders portions of the vessel, so that the skirt edge 34 provides a leak-tight sealing of the film, to prevent any egress of gas.

Accordingly, the heat shrink film may be selected to provide suitable gas permeability characteristics with respect to the contained gas, so that diffusion through the film is precluded, or otherwise controlled at a minimal level.

As a further expedient, the film may be formed as a multi-layer laminate, having one or more layers serving to provide diffusional and permeation resistance to the overall film, and permitting the colorimetric change of the film structure to be readily visually perceived by an observer.

Figure 2:
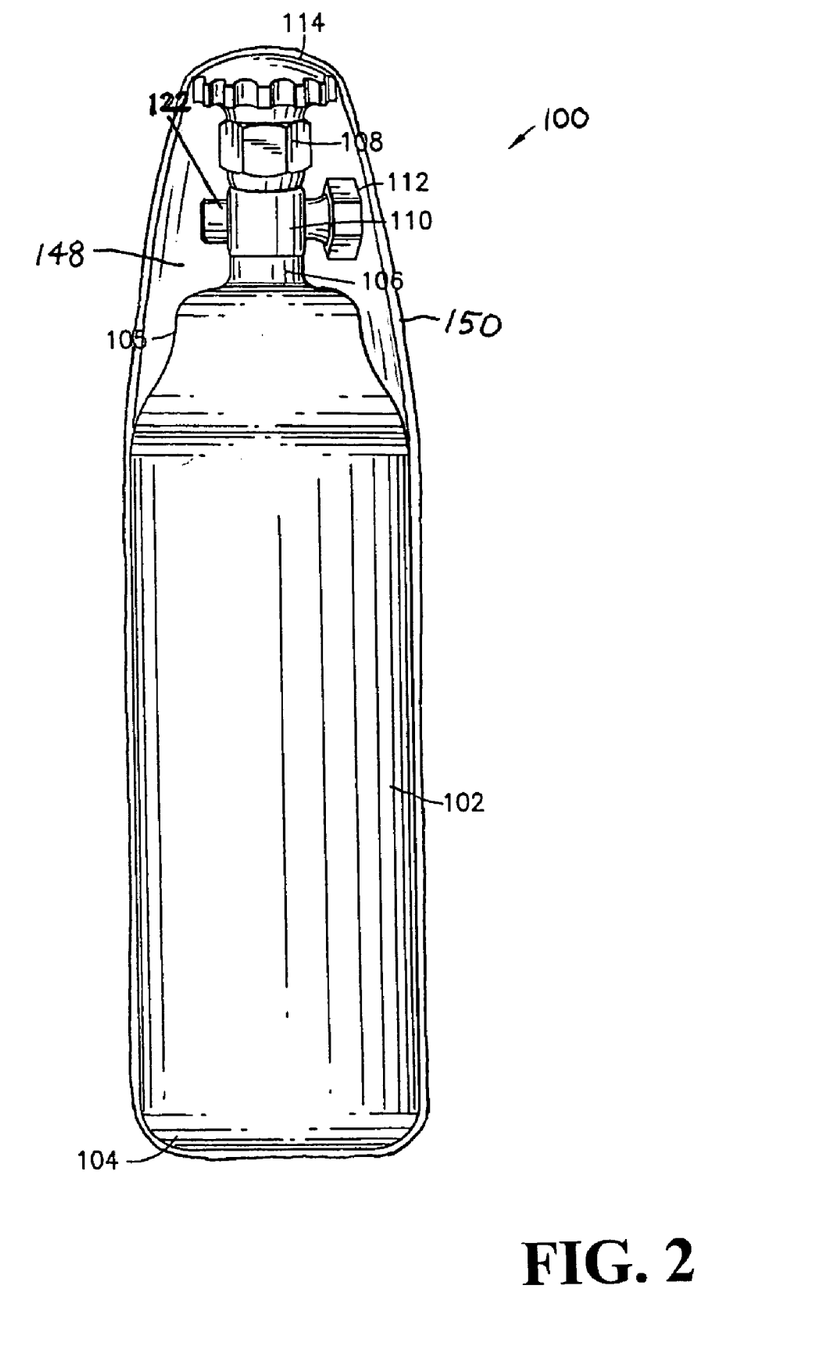
FIG. 2 is a front elevation view of a fluid storage and dispensing vessel shrink-wrapped in a colorimetric film, according to another embodiment of the invention.

Referring now to FIG. 2, there is shown a perspective view of a fluid storage and dispensing vessel 100 according to another embodiment of the invention.

The storage and dispensing vessel 100 comprises a cylinder 102 of elongate character having an upper portion 105 including neck 106, and a lower portion 104 having a flat bottom so that the cylinder may be reposed in vertically upstanding relationship on a support surface.

Coupled to the neck 106 of the cylinder 102 is a manual or automated (by electrical or air means) high pressure stainless steel diaphragm valve 108 comprising a valve body 110 which is secured to the neck 106 of cylinder 102 in any suitable manner, as for example by means of complimentarily matable threading on the respective engaging surfaces of the valve body 110 and neck 106, as augmented by thread-locking adhesive, sealant, or other medium applied to the threaded surfaces and serving to ensure gas-impermeability and leak-tightness of the completed assembly.

The valve 108 comprises a manual actuator handle 114 which may be manually rotated to open or close the valve. The valve body 110 is connected to a discharge flange coupling 112, by means of which the storage and dispensing vessel can be joined to suitable dispensing assembly means comprising piping, tubing, conduits, instrumentation, mass flow controllers, flow regulators of other types, purifiers, filters, etc. The valve 108 may optionally be pneumatically activatable.

The valve body 110 as shown is joined to a burst disk 122.

As illustrated, the storage and dispensing vessel 100 is fully enshrouded by a shrink-wrap film 150, to form an enclosed interior volume 148 at the upper portion of the vessel, overlying the valve body and valve and actuator handle.

The shrink-wrap film 150 may have impregnated therein or otherwise associated with the film a suitable colorimetric agent that in exposure to leakage of fluid from the cylinder 102 undergoes a visually discernable color change, thereby alerting the observer that a leakage event has occurred.

Figure 3:
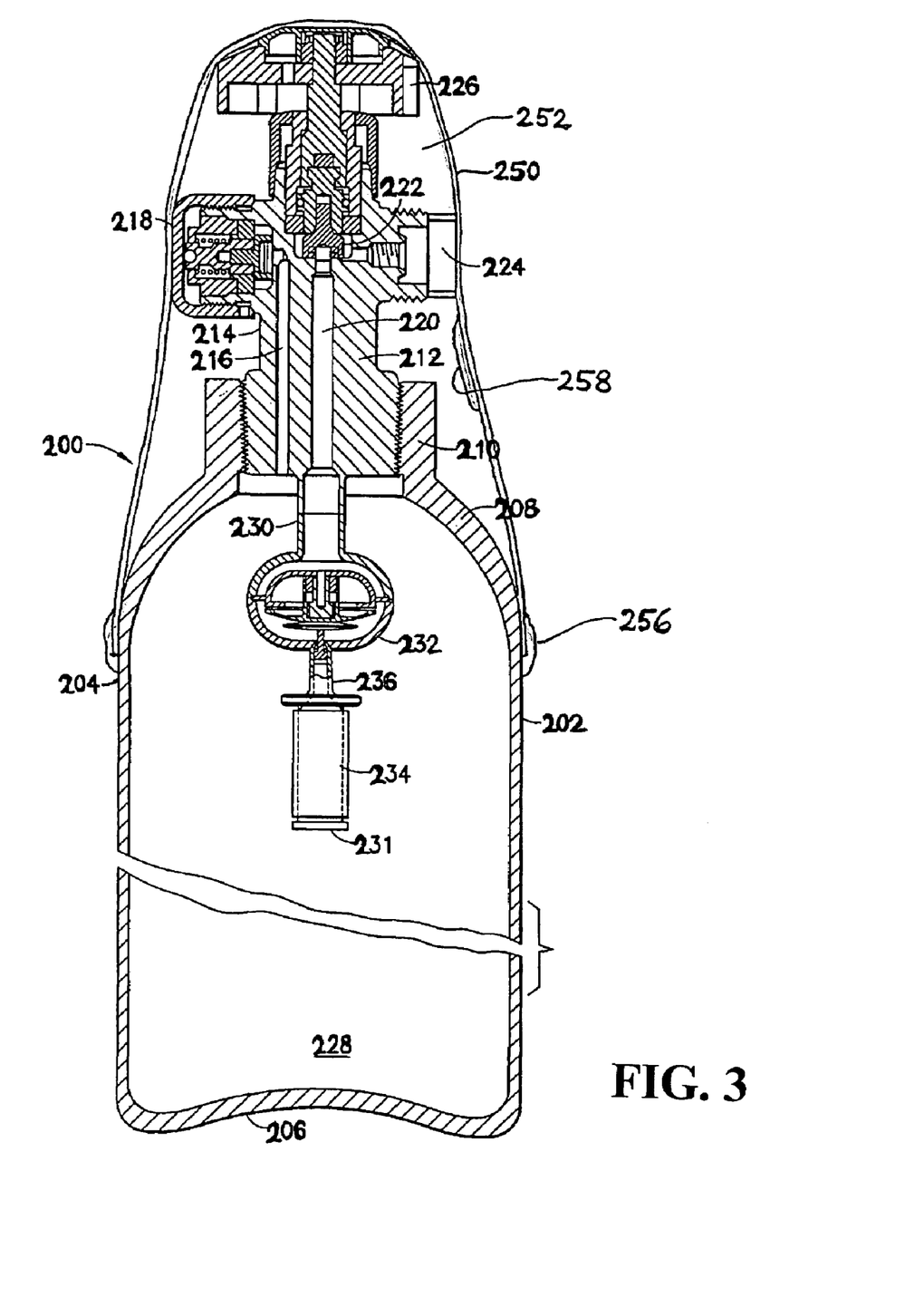
FIG. 3 is a front sectional elevation view of a fluid storage and dispensing vessel according to yet another embodiment of the invention, wherein the valve head and neck area of the vessel are shrink-wrapped with a colorimetric indicating film, according to a further embodiment of the invention.

FIG. 3 is a schematic cross-sectional elevation view of one gas storage and dispensing system 200 according to yet another illustrative embodiment of the invention. The system 200 includes a fluid storage and dispensing vessel 202 of generally cylindrical form, with a cylindrical sidewall 204 closed at its lower end by floor member 206. At the upper end of the vessel is a neck 208 including a cylindrical collar 210 defining and circumscribing a top opening (port) of the vessel. The vessel wall, floor member and neck thereby enclose an interior volume 228, as shown.

At the neck of the vessel, a threaded plug 212 of the valve head assembly 214 is threadably engaged with the interior threaded opening of the collar 210. The valve head assembly 214 includes a central fluid flow passage 220 joined in fluid flow communication with a central working volume cavity in the valve head assembly. The central working volume cavity in turn is joined to outlet 224, which may be exteriorly threaded or otherwise constructed for attachment of a connector and associated piping, conduit, etc. thereto.

Disposed in the central working volume cavity is a valve element 222 that is joined to a hand wheel 226 in the embodiment shown, but may alternatively be joined to an automatic valve actuator or other controller or actuating means.

The valve head assembly 214 also features in the valve block a fill passage 216 communicating with fill port 218 and the interior volume 228 of the vessel. The vessel 202 may thereby be charged with pressurized gas, following which the fill port is closed and capped, as shown.

The central fluid flow passage 220 in the valve head assembly 214 is joined at its lower end to a connector flow tube 230, which in turn is joined to the regulator 232. The regulator is set to maintain a selected pressure of the fluid discharged from the vessel.

At the lower end of the regulator is joined a tubular fitting 236 which in turn is joined, e.g., by butt welding, to a filter unit 234 having a diffuser end cap 231 at its lower extremity. The filter unit may be formed of stainless steel, with the diffuser wall being formed of a sintered stainless steel such as 316L stainless steel. The filter unit has a wall porosity that permits removal of all particles greater than a predetermined diameter, e.g., greater than 0.003 micrometers at 30 standard liters per minute flow rate of gas from the system. Filter units of such type are commercially available from Mott Corporation (Farmington, Conn.).

In use, a pressurized gas is contained in the interior volume 228 of the vessel 202. The gas pressure regulator 232 is set to a selected set point to provide flow of dispensed gas when the valve in the valve head assembly 214 is opened, with the gas flowing through the filter unit 234, fitting 236, regulator 232, connector flow tube 230, central fluid flow passage 220 in the valve head assembly 214, the central working volume cavity, and outlet 224. The valve head assembly may be joined to other piping, conduits, flow controllers, monitoring means, etc. as may be desirable or required in a given end use application of the invention.

Heat-shrink film 250 is wrapped on the vessel to shroud the upper portion of the fluid storage and dispensing vessel 202. By such shrink-wrapping, the shoulder region of vessel 202, the neck portion of the vessel and the valve head assembly are enclosed by the shrink-wrap film 250, in the interior volume 252 overlaid by the film.

In this embodiment, the lower portion of the shrink-wrap film 250 is sealed to the exterior surface of the cylinder sidewall by a sealant 256. The sealant 256 may be of any suitable type, such as a low-tack adhesive medium, caulk, putty, or other suitable medium that is effective to leak-tightly seal the lower skirt edge portion of the heat-shrink film to the exterior side wall surface, about the full circumference of the vessel.

The film 250 may be impregnated or otherwise associated with or contain a suitable colorimetric agent that is effective in exposure to fluid leakage from vessel 202 to undergo a color change that is visually discernable by an observer.

As a further optional modification, the shrink-wrap film 250 may have on an interior surface thereof a getter material 258, for chemisorption and removal of leakage gas from the interior volume 252 within the shrink-wrap film 250.

The getter may be of any suitable type, which is chemisorbently effective for removal of the specific fluid contained in vessel 202. By way of specific example, the getter material 258 may comprise a thin film of calcium, barium or magnesium, that will react with the fluid in vessel 202 when same leaks into the interior volume 252, e.g., a fluid such as a hydride or halide gas. The getter material 258 may as shown be localized as a discrete mass on the interior surface of the shrink-wrap film, or alternatively the getter may be provided as a flashed thin film on the surface, at sufficient concentration to effectively remove leaking gas. As a still further alternative, the getter material may be provided on an exterior surface of the neck or shoulders region of the vessel, within the interior volume 252.

The getter material 258 therefore is effective to remove the leakage gas, so that same does not pose a health or safety issue. The shrink-wrap film 250, when a getter material is employed, can be applied under inert atmosphere, so as to preclude the premature reaction of the chemisorbent material with atmospheric or other ambient gases that could otherwise deplete the capability of the getter for subsequent removal of leaking gas from the vessel.

In use, leaking gas would therefore contact the shrink-wrap film 250, which would responsively undergo a colorimetric change visually perceptible to an observer, to evidence the occurrence of the leakage event. Concurrently, the leaked gas would contact the getter material 258 and be taken up, so that the vessel thereafter can be more readily handled for isolation, quarantine, reworking or other disposition.

With reference to the FIG. 3 embodiment, the sealant 256 is an optional feature, which may be superfluous if the shrink-wrap film is sufficiently adherent and sufficiently shrunk to compressively self-seal at the lower skirt edge of the film. Alternatively, a tape or elastic sealing band may be employed in lieu of the sealant 256.

Although the invention has been described herein with respect to illustrative embodiments, and with reference to specific aspects and features, it will be recognized that the invention is susceptible to variations, modifications and other embodiments as will readily suggest themselves to those of ordinary skill in the art, based on the disclosure herein. Accordingly, the invention is intended to be broadly interpreted and construed, as encompassing such variations, modifications and alternative embodiments, within the spirit and scope of the claims hereafter set forth.

What is claimed is:

1. A fluid storage and dispensing apparatus comprising a fluid storage and dispensing vessel including a neck portion and a valve head assembly attached to said vessel at said neck portion, and a shrink-wrapped colorimetric film effective in the presence of leaking gas from said vessel to undergo a color change indicative of said leaking gas, said shrink-wrapped colorimetric film being sealed to an exterior surface of the vessel and overlying the neck portion of the vessel and the valve head assembly to define an interior void volume enclosed by the shrink-wrapped film, wherein said enclosed interior void volume surrounds the neck portion and valve head assembly, whereby gas leakage at said neck portion or at said valve head assembly can enter the enclosed interior void volume and distribute throughout said enclosed interior void volume to effect a color change in the shrink-wrapped film surrounding the neck portion and valve head assembly, thereby providing a visually perceptible response to a leakage event.

2. The fluid storage and dispensing apparatus of claim 1, wherein said film comprises a poly(vinylpyridine) film.

3. The fluid storage and dispensing apparatus of claim 2, wherein said fluid storage and dispensing apparatus contains tris(trifluoromethyl)stibine.

4. The fluid storage and dispensing apparatus of claim 1, wherein said film comprises a polyvinylalcohol film having copper sulfate incorporated therein.

5. The fluid storage and dispensing apparatus of claim 1, wherein the fluid storage and dispensing vessel comprises a valve head and said valve head is shrink-wrapped in said film.

6. The fluid storage and dispensing apparatus of claim 1, wherein the entire fluid storage and dispensing vessel is shrink-wrapped in said film.

7. The fluid storage and dispensing apparatus of claim 1, wherein the fluid storage and dispensing vessel contains tris(trifluoromethyl)stibine.

8. The fluid storage and dispensing apparatus of claim 1, wherein the fluid storage and dispensing vessel contains an organometallic compound.

9. The fluid storage and dispensing apparatus of claim 1, wherein said film contains iron oxide.

10. The fluid storage and dispensing apparatus of claim 1, wherein an upper portion of the fluid storage and dispensing vessel is shrink-wrapped in said film.

11. The fluid storage and dispensing apparatus of claim 1, wherein said film contains copper sulfate.

12. The fluid storage and dispensing apparatus of claim 1, wherein said film contains copper hydroxide.

13. The fluid storage and dispensing apparatus of claim 1, wherein said film comprises a material selected from the group consisting of polyethylene, polyolefin, polyvinyl chloride and polyester.

14. The fluid storage and dispensing apparatus of claim 1, wherein said film comprises a polyvinyl chloride film.

15. The fluid storage and dispensing apparatus of claim 1, wherein the fluid storage and dispensing vessel contains a semiconductor manufacturing reagent.

16. The fluid storage and dispensing apparatus of claim 1, wherein said film has a getter associated therewith.

17. The fluid storage and dispensing apparatus of claim 16, wherein the getter is on an interior surface of said film.

18. The fluid storage and dispensing apparatus of claim 16, wherein the getter is disposed on an exterior surface of the fluid storage and dispensing vessel, in an interior volume enclosed by said film.

19. A method of visually detecting a leakage event associated with a fluid storage and dispensing vessel including a neck portion and a valve head assembly attached to said vessel at said neck portion, said method comprising shrink-wrapping at least a portion of said vessel with a colorimetric film effective in the presence of leaking gas from said vessel to undergo a color change indicative of said leaking gas, and sealing the colorimetric film to an exterior surface of the vessel so that the colorimetric film overlies the neck portion of the vessel and the valve head assembly to define an interior void volume enclosed by the colorimetric film, with the colorimetric film surrounding the neck portion and valve head assembly, whereby gas leakage at said neck portion or at said valve head assembly can enter the enclosed interior void volume and distribute throughout said enclosed interior void volume to effect a color change in the colorimetric film surrounding the neck portion and valve head assembly, thereby providing a visually perceptible response to a leakage event.

20. The method of claim 19, wherein said shrink-wrapping comprises heat-shrinking said film against said vessel.

21. The method of claim 19, wherein said film comprises a poly(vinylpyridine) film.

22. The method of claim 19, wherein said fluid storage and dispensing apparatus contains tris(trifluoromethyl) stibine.

23. The method of claim 19, wherein said film comprises a polyvinylalcohol film having copper sulfate incorporated therein.

24. The method of claim 19, wherein said fluid storage and dispensing vessel comprises a valve head and said valve head is shrink-wrapped in said film.

25. The method of claim 19, wherein the entire fluid storage and dispensing vessel is shrink-wrapped in said film.

26. The method of claim 19, wherein the fluid storage and dispensing vessel contains tris(trifluoromethyl) stibine, and said film comprises a poly(vinvlpyridine) film.

27. The method of claim 19, wherein the fluid storage and dispensing vessel contains an organometallic compound.

28. The method of claim 19, wherein said film contains iron oxide.

29. The method of claim 19, wherein an upper portion of the fluid storage and dispensing vessel is shrink-wrapped in said film.

30. The method of claim 19, wherein said film contains one of copper sulfate and copper hydroxide.

31. The method of claim 19, wherein said film comprises a material selected from the group consisting of polyethylene, polyolefin, polyvinyl chloride and polyester.

32. The method of claim 19, wherein said film comprises a polyvinyl chloride film.

33. The method of claim 19, wherein said storage and dispensing vessel contains a semiconductor manufacturing reagent fluid.

34. The method of claim 19, wherein said film has a getter associated therewith.

35. The method of claim 34, wherein the getter is on an interior surface of said film.

36. The method of claim 34, wherein the getter is disposed on an exterior surface of the fluid storage and dispensing vessel, in an interior volume enclosed by said film.

37. A fluid storage and dispensing apparatus, comprising a fluid storage and dispensing vessel having at least a portion thereof shrink-wrapped in a film in a compressive state against adjacent exterior surface of the vessel, wherein said shrink-wrapped film encloses or constitutes a colorimetric member effective in exposure to fluid leaking from the vessel to change color, thereby providing a visually perceptible response to a leakage event, wherein said fluid storage and dispensing apparatus comprises at least one of the features (a)-(c):
  (a) said fluid storage and dispensing vessel containing tris(trifluoromethyl)stibine;
  (b) said shrink-wrapped film containing copper sulfate; and
  (c) said shrink-wrapped film containing copper hydroxide.

38. A method of visually detecting a leakage event associated with a fluid storage and dispensing vessel, said method comprising shrink-wrapping at least a portion of said vessel in a film so that said film is in a compressive state against adjacent exterior surface of the vessel, wherein said shrink-wrapped film encloses or constitutes a colorimetric member effective in exposure to fluid leaking from the vessel to change color, thereby providing a visually perceptible response to a leakage event, wherein said method is characterized by at least one of the features (a)-(c):
  (a) said fluid storage and dispensing vessel containing tris(trifluoromethyl)stibine;
  (b) said shrink-wrapped film containing copper sulfate; and
  (c) said shrink-wrapped film containing copper hydroxide.

* * * * *